ative Examiner—George Yanulis
United States Patent [19]
Hino

[11] Patent Number: 4,466,804
[45] Date of Patent: Aug. 21, 1984

[54] EXTRACORPOREAL CIRCULATION OF BLOOD

[76] Inventor: Tsunekazu Hino, 2513, Hino, Hino-shi, Tokyo, Japan

[21] Appl. No.: 305,381

[22] Filed: Sep. 24, 1981

[51] Int. Cl.³ .............................................. A61M 1/03
[52] U.S. Cl. ................................. 604/4; 128/DIG. 3; 422/44; 422/45; 604/31; 604/118
[58] Field of Search ............. 128/1 D, 214 R, 214 E, 128/214 F, 675, 748, DIG. 3, DIG. 12, DIG. 13, DIG. 14; 422/44, 45, 46, 47, 48; 604/4–6, 7, 118, 121, 31

[56] References Cited

U.S. PATENT DOCUMENTS

| | | | |
|---|---|---|---|
| 3,590,809 | 7/1971 | London | 128/DIG. 13 |
| 3,890,969 | 6/1975 | Fischel | 128/214 R |
| 3,946,731 | 3/1976 | Lichtenstein | 128/214 E |
| 4,175,264 | 11/1979 | Schiff | 128/1 D |
| 4,231,354 | 11/1980 | Kurtz et al. | 128/1 D |

OTHER PUBLICATIONS

Peter J. Martin, "New Controller for In-Series Cardiac-Assist Devices", pp. 243–249.

Primary Examiner—Kyle L. Howell
Assistant Examiner—George Yanulis
Attorney, Agent, or Firm—Armstrong, Nikaido, Marmelstein & Kubovcik

[57] ABSTRACT

An extracorporeal blood circulation system including a line for withdrawing the venous blood from the patient, an artificial lung provided on the line, a reservoir for the blood withdrawn, a blood supply line for sending out the blood from the reservoir to the artery of the patient, and a blood supply pump provided on the blood supply line and serving as an artificial heart. The amount of blood to be supplied is automatically controlled to maintain the arterial pressure of the patient in a suitable required range. The blood supply pump is stopped when the arterial pressure of the patient measured is above a predetermined upper limit value, while the pump is driven when the arterial pressure has lowered to a level below a lower limit value. The amount of blood to be withdrawn is also controlled automatically to keep the central venous pressure of the patient approximately constant. The blood withdrawing line has a blood withdrawing pump. The reservoir is connected to the inlet side of this pump by a shunt line having a valve which is usually opened. The valve is closed when the central venous pressure exceeds a predetermined upper limit level. A vertical overflow tube detects the central venous pressure exceeding the upper limit level.

18 Claims, 8 Drawing Figures

EXTRACORPOREAL CIRCULATION OF BLOOD

BACKGROUND OF THE INVENTION

The present invention relates to a system for the extracorporeal circulation of the blood for a patient undergoing an operation on the lung or heart to refresh the blood of the patient and always circulate the blood through the body in place of the lungs and heart of the patient.

Systems for extracorporeally circulating the blood comprise a blood withdrawing line for drawing off the venous blood from the patient, an artificial lung provided on the line, a reservoir for the withdrawn blood, a blood supply line for feeding the blood from the reservoir to the artery of the patient, and a blood supply pump provided on the blood supply line and serving as an exteriorly positioned heart. With such systems, it is most critical to maintain the amount of the blood withdrawn from the body of the patient in balance with the supply of the blood to the body to keep the amount of the blood circulated through the body constant at all times. In controlling the amount of blood circulation through the body, bleeding from the site operated on, etc. must also be considered since bleeding reduces the amount of blood in the body. Conventionally the amount of blood circulation through the body is controlled by the operator through manual procedures for driving the blood withdrawing pump and blood supply pump and replenishing the blood reservoir with transfusion blood. This mode of control involves many items of manipulation, and the system must be controlled itemwise promptly based on immediate judgment while watching incessantly changing conditions of the patient, i.e. arterial and venous blood pressures, measurement of amount of bleeding, amount of blood in the reservoir and electrocardiogram. Thus the operator must be trained for controlling the system. Additionally the operator suffers from much fatigue when the operation takes a prolonged period of time.

SUMMARY OF THE INVENTION

An object of the present invention is to provide a system for the extracorporeal circulation of the blood which is adapted to automatically control the blood supply to the body so that the arterial pressure will be maintained suitably in a required range.

Another object of the invention is to automatically control the amount of blood to be withdrawn from the body so that the venous pressure of the patient will be maintained at an approximately constant level.

Another object of the invention is to provide a system for the extracorporeal circulation of the blood which is adapted to control the amount of blood to be supplied to the body of the patient and the amount of blood to be withdrawn therefrom to keep the amount of circulation of the blood through the body approximately constant.

Another object of the invention is to smoothly effect a change from the spontaneous circulation of the blood by the cardiac force of the patient to the forced circulation of the blood by an extracorporeal system or a change reverse to the above.

Another object of the invention is to assist the intracorporeal circulation of the blood by an extracorporeal circulation system while the blood is being spontaneously circulated through the body by the cardiac force of the patient so that the intracorporeal circulation of the blood will not be interrupted even when the heart stops temporarily.

The system of this invention for the extracorporeal circulation of the blood comprises a blood withdrawing line, an artificial lung provided on the line, a reservoir for the blood withdrawn, a blood supply line for sending out the blood from the reservoir, a blood supply pump provided on the blood supply line and serving as an exteriorly positioned heart, means for detecting that the venous pressure has exceeded a predetermined upper limit level, a blood pressure transducer for measuring the arterial pressure, means for increasing the amount of blood to be withdrawn when the venous pressure has exceeded the upper limit level, and means for controlling the blood supply pump in response to an output from the blood pressure transducer to maintain the arterial pressure in a predetermined required range.

The venous pressure detecting means comprises a vertical tube having an upper end opened to the atmosphere and a blood sensor provided at a position of specified height for the vertical tube for detecting that the blood level has reached the position. This arrangement detects the venous pressure more accurately than a blood pressure transducer used as the venous pressure detecting means. For the same purpose, two vertical tubes may be used which are in communication with each other at upper portions thereof. When the blood in one of the vertical tubes rises beyond the communicating portions, the blood flows over this portion into the other tube. The overflow is detected by a sensor. If the vertical tube or sensor is movable upward or downward, the upper limit level of the venous pressure is variable. The venous pressure to be detected is preferably the central venous pressure.

The means for controlling the blood supply pump preferably comprises an upper limit detecting circuit for detecting that the arterial pressure has exceeded a predetermined upper limit value, a lower limit detecting circuit for detecting that the arterial pressure has been lowered below a predetermined lower limit value, and a control circuit for stopping the blood supply pump upon detecting the upper limit and for operating the blood supply pump upon detecting the lower limit. It is preferable to use a pulsatile pump as the blood supply pump.

Other features and advantages of this invention will become apparent from the following description of an embodiment with reference to the accompanying drawings.

DESCRIPTION OF THE PREFERRED EMBODIMENT

Figure 1:
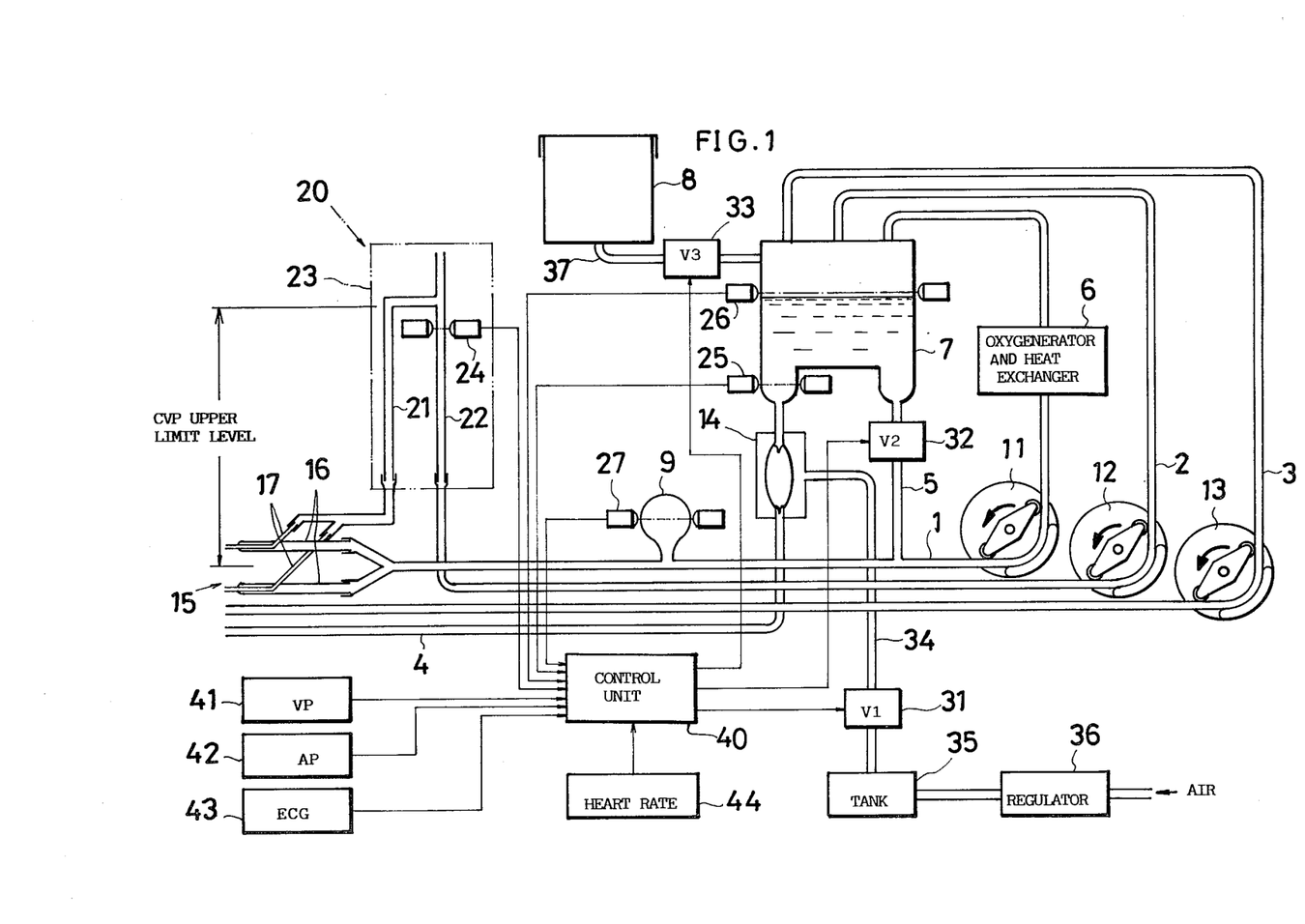
FIG. 1 is a diagram of a preferred embodiment of the invention showing a circuit for extracorporeal blood circulation and including a block diagram of part of the electric circuit associated with the circuit.

The system of this invention for extracorporeal blood circulation includes a blood withdrawing line 1, an overflow line 2, an aspiration line 3 and a blood supply line 4. These lines 1 to 4 are each made of a flexible tube. The lines 1 to 3 are provided with rotary pumps 11 to 13 respectively. The rotary pump comprises rollers adapted for a circular motion to draw and forward the blood through the tube by squeezing the tube, forming a continuous flow of blood. The line 4 is provided with a pulsatile pump 14 which is operated by compressed air supplied thereto intermittently to intermittently force the blood through the line 4 as a pulsating flow.

Figures 3, 4, 5:
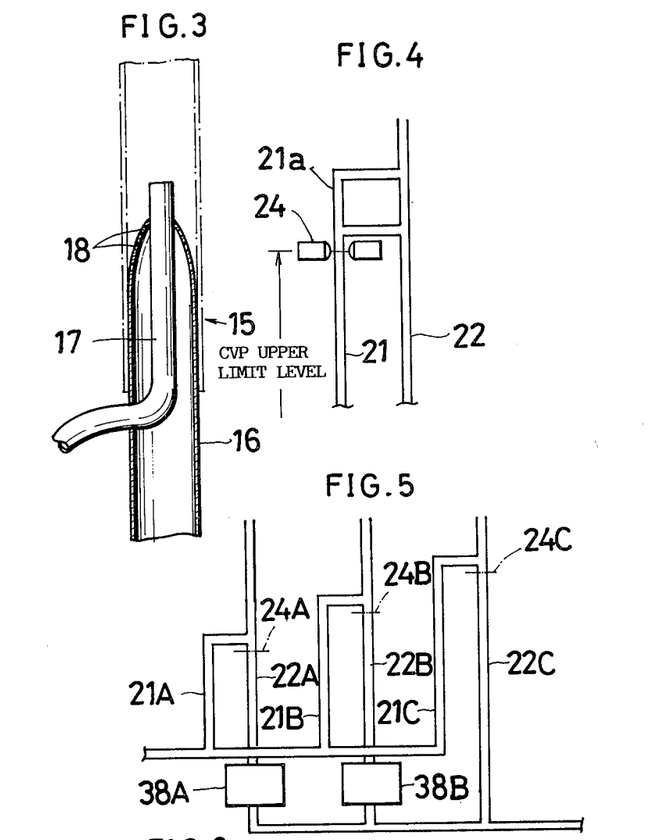
FIG. 3 is a sectional view showing a cannula.
FIGS. 4, 5 and 6 show other examples of central venous pressure adjusting units.

The line 1 for withdrawing the venous blood from the body of the patient has two cannulas 15 connected to one end thereof. As seen in FIG. 3, the cannula 15 comprises an outer tube 16 having a slightly tapered forward end, and an inner tube 17 having a forward end projecting outward from the forward end of the outer tube 16 and a rear end extending outward from the outer tube 16. The forward end of the outer tube 16 is formed with a large number of holes 18. The rear end of the outer tube 16 is connected to the line 1. The forward ends of the cannulas 15 are inserted into the superior and inferior venae cavae of the patient individually to draw the venous blood into the line 1 through the holes 18 and the outer tubes 16. The line 1 is provided with an oxygenator and a heat exchanger 6. The oxygenator functions as an artificial lung, in which the venous blood withdrawn from the body of the patient gives off carbon dioxide and takes up oxygen. The heat exchanger maintains the blood at the desired temperature and, when needed, lowers the blood temperature. The blood thus refreshed is led into a blood reservoir 7 and stored therein. Alternatively the heat exchanger may be disposed between the reservoir 7 and the pump 14 on the blood supply line 4, or on a portion of the line 4 downstream from the pump 14. A collapsible bag 9 for checking whether or not the blood is being withdrawn smoothly is provided on the blood withdrawing line 1 at a location between the shunt line 5 to be described later and the cannulas 15. When the withdrawn blood is flowing smoothly through the line 1, the bag 9 is filled with the blood and is thereby inflated. If the line 1 is collapsed somewhere between the cannulas 15 and the bag 9, or if the blood is not withdrawn from the body for one reason or another, no blood is supplied to the bag 9. Since the blood in the line 1 is drawn by the pump 11 which is in operation at all times, the bag 9 is emptied of the blood and collapses. A sensor 27 is provided for detecting the state of the bag 9, i.e. whether the bag 9 is inflated or collapsed. The detecting signal of the sensor 27 is fed to a control unit 40. If the bag 9 collapses, an alarm goes on, informing the operator of the trouble occurring in the blood withdrawing line 1. When necessary, the blood supply pump 14 may be brought out of operation in the event of the line 1 malfunctioning. In the present embodiment, however, the pump 14 need not be stopped even if the line 1 is blocked since the blood is withdrawn through the overflow line 2 provided in parallel with the line 1.

A bottom portion of the blood reservoir 7 is connected by a shunt line 5 to a portion of the line 1 upstream from the pump 11. The line 5 has an electromagnetic valve 32. The valve 32 and the electromagnetic valve 33 to be described later are each a pinch valve. When the valve 32 is open, the blood in the reservoir 7 is aspirated by the pump 11 through the line 5 and returned to the reservoir 7 by way of the oxygenator and heat exchanger 6. Since a major portion of the blood drawn and forwarded by the pump 11 is supplied via the line 5, the amount of venous blood withdrawn from the body is small when the valve 32 is open. When the valve 32 is closed, no blood is supplied through the line 5, with the result that the suction by the pump 11 acts entirely on the cannula 15 to withdraw an increased amount of venous blood from the patient.

The overflow line 2 is provided with a unit 20 for adjusting the central venous pressure (hereinafter referred to as "CVP"), which is the mean pressure of the superior vena cava pressure and the inferior vena cava pressure and is given by the inner tubes 17 of the pair of cannulas 15. The CVP adjusting unit 20 comprises a support member 23 the position of which is vertically adjustable, nd two vertical tubes 21 and 22 mounted on the support member 23. The vertical tube 21 is connected at its lower end to the inner tubes 17 of the two cannulas 15, while the lower end of the other vertical tube 22 is in communication with the inlet of the pump 12. The upper end of the vertical tube 21 communicates through a horizontal tube with an upper portion of the vertical tube 22, which has an upper end extending upward beyond the communicating portion and opened to the atmosphere. A sensor 24 for detecting an overflow of blood is disposed at a location slightly below the communicating portion of the vertical tube 22. Each of the sensor 24, the above-mentioned sensor 27, and the sensors 25, 26 to be described later is a photoelectric detector, for which infrared rays are preferably used as the beam to be projected. Other sensors, such as those utilizing ultrasonic waves or capacitance, are of course usable.

Since the forward ends of the inner tubes 17 of the cannulas 15 are inserted into the superior and inferor venae cavae individually as already stated, portions of the venous blood flow into the inner tubes 17 individually from the two venae cavae and join together, whereby the blood pressures of the two veins are averaged. The venous blood rises through the vertical tube 21 in accordance with the mean blood pressure, i.e. the CVP. The level of the blood in the vertical tube 21 represents the CVP. The upper limit level of CVP is determined by the height of the upper end of the vertical tube 21 from the heart of the patient. When the CVP is higher than the upper limit level, the blood within the vertical tube 21 overflows the tube 21 into the vertical tube 22, so that this is detected by the sensor 24. The overflow of blood is aspirated by the pump 12 and led into the reservoir 7. The upper limit level of CVP can be set to a desired value by adjusting the level of the support member 23.

The aspiration line 3 is provided for aspirating the blood released from the site of the patient operated on. The blood is sent to the reservoir 7 by the pump 13. The blood through the lines 2 and 3, although led directly into the reservoir 7 in FIG. 1, may be fed to the oxygenerator and heat exchanger 6 and then forwarded to the reservoir 7 when so required.

The blood supply line 4 has one end connected to a bottom portion of the reservoir 7 and the other end connected to a cannula which is inserted into the ascending aorta of the patient. The refreshed blood stored in the reservoir 7 is passed through the line 4 into the aorta by the pulsatile pump 14 which is an artificial heart. The blood through the line 4 is in effect pulsatile and therefore resembles the arterial blood forced out from the heart to produce a physiologically favorable influence on the patient. A reservoir 8 disposed above the blood reservoir 7 for storing the blood to be transfused has a bottom portion connected to an upper portion of the reservoir 7 by a tube 37. The tube 37 has an electromagnetic valve 33. The sensor 25 detects that only a small amount of blood remains in the reservoir 7, while the sensor 26 detects that the reservoir 7 is filled with the blood to its upper limit level. When the small amount of blood remaining in the reservoir 7 is detected by the sensor 25, the electromagnetic valve 33 is opened to supply the blood from the reservoir 8. When the sensor 26 detects that the reservoir 7 has been filled with the blood to its upper limit level, the valve 33 is closed to discontinue the supply of blood. The blood in the reservoir 8 may be supplied to the reservoir 7 by way of the oxygenerator and heat exchanger 6. The reservoir 8 may be connected to the aspiration line 3. Ringer's solution and other solutions or drugs needed for the patient under operation are admixed with the blood in the reservoir 7. Preferably an artificial kidney (not shown) is provided for filtering off such components from the blood in the reservoir 7 when the blood is diluted with these solutions to an excessive volume.

The compressed air for driving the pulsatile pump 14 is supplied from an air source through a line 34, which is provided with a pressure regulator 36, tank 35 and electromagnetic valve 31. As will be stated later, the valve 31 is controlled to open and close intermittently.

The control unit 40 controls the electromagnetic valves 31, 32 and 33. The unit 40 receives detecting signals from the sensors 24, 25, 26 and 27, output signals from blood pressure transducers 41 and 42 for detecting the venous blood pressure and the arterial blood pressure (hereinafter referred to as "VP" and "AP" respectively of the patient, output signals from an electrocardiograph 43 for preparing an electrocardiogram for the patient, and output pulses from a heat rate generator 44. The blood pressure transducers 41 and 42 measure the blood pressures of the vena cava and the aorta respectively. When desired, the blood pressures of the superior and inferor venae cavae may be measured individually, and the mean value of the measurements may be used as the VP (i.e. CVP).

Figure 2:
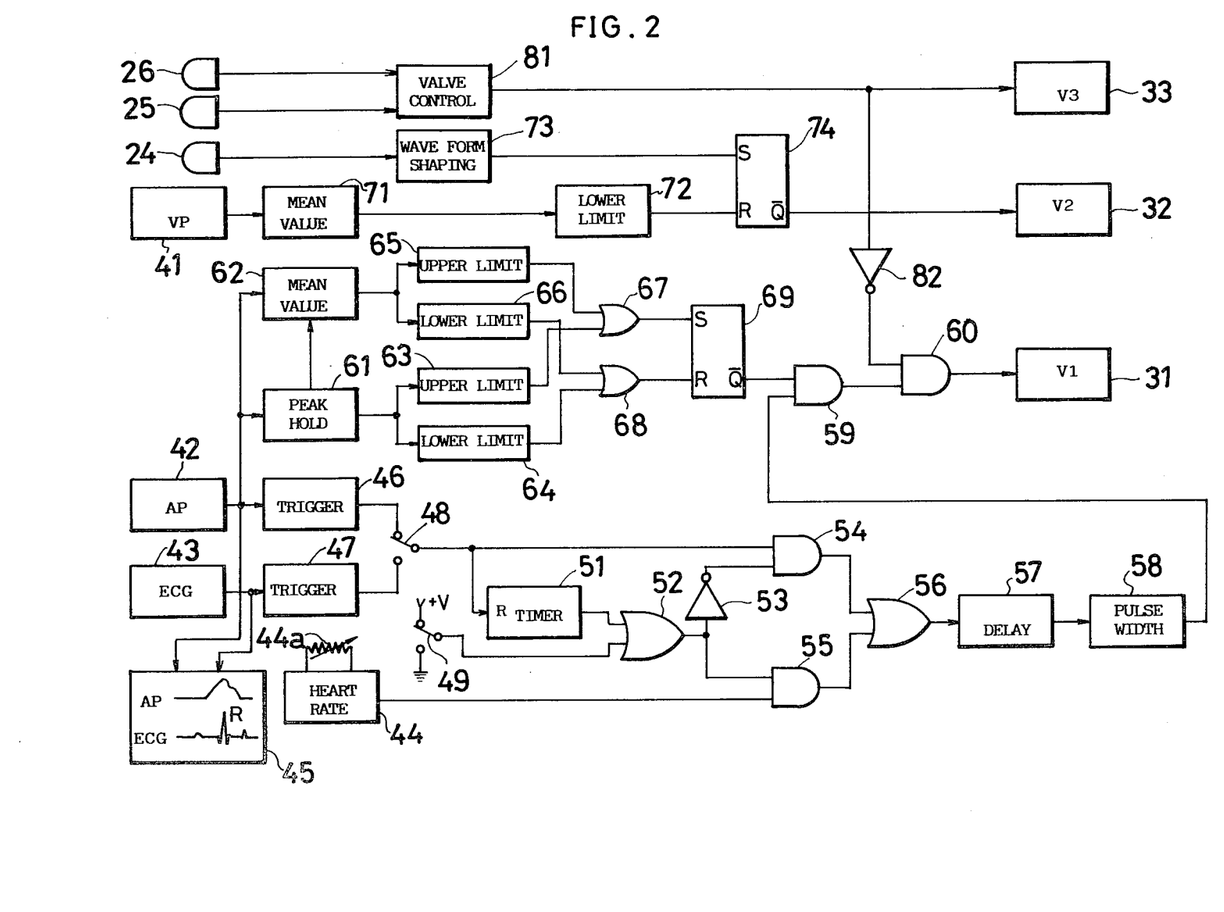
FIG. 2 is a block diagram showing the construction of a control unit in detail.

FIG. 2 shows the construction of the control unit 40 in detail. The signals of the transducer 42 representing the AP and those of the electrocardiograph 43 are sent to a monitor 45 equipped with a cathode-ray tube (CRT), on which the waveform of AP and the electrocardiogram are displayed. While the heart of the patient is in operation, the blood is circulated through the body by the force of cardiac contraction. This mode of blood circulation is termed "spontaneous circulation." On the other hand, the intracorporeal circulation of the blood by the extracorporeal system of this invention, particularly by the pulsatile pump 14, is termed "forced circulation." The forced circulation can be effected by the pump 14 also during the spontaneous circulation because there is the need to assist in the blood circulation by the pump 14 when the spontaneous circulation is to be changed over to the forced circulation and vice versa, whereby the change-over can be accomplished smoothly. The AP signal from the blood pressure transducer 42 and the output signal from the electrocardiograph 43 are used as triggers for starting the pump 14 during the spontaneous circulation. A trigger generating circuit 46 produces a trigger pulse when the AP signal waveform has reached a peak. A trigger generating circuit 47 produces a trigger pulse upon the rise of R wave in the electrocardiogram. With reference to the AP waveform and electrocardiogram on the monitor 45, the operator can select one of the two trigger pulses by a selecting switch 48. The selected trigger pulse is sent to an AND circuit 54 and to a timer 51.

For the forced circulation, the heart rate generator 44 produces trigger pulses of frequency set by its setting device 44a. The heart rate can be set as desired by the setting device 44a. The trigger pulse from the generator 44 is fed to an AND circuit 55. A switch 49 is used for setting the forced circulation. When the forced circulation is set by the switch 49, a high (H) level signal is given to an OR circuit 52.

It is likely that the heart of the patient will stop temporarily without undergoing periodic contraction when spontaneous circulation is changed to forced circulation and vice versa. If the heart fails to function for spontaneous circulation, the blood will not circulate through the body, so that the circulation mode must be changed over to forced circulation temporarily. The timer 51 is reset by the trigger pulse of the generating circuit 46 or 47. If the timer 51 is not reset again upon lapse of a predetermined period of time, e.g. 2 seconds, after resetting, the timer produces an H level signal, which is fed to the OR circuit 52. When forced circulation is set by the switch 49, or when the heart of the patient does not repeat contraction even upon the lapse of 2 seconds, the OR circuit 52 produces an H level signal, which is delivered to the AND circuit 55. Accordingly the trigger pulse from the heart rate generator 44 passes through the AND circuit 5 and then through an OR circuit 56 and is fed to a delay circuit 57. The H level signal from the OR circuit 52 is inverted by a NOT circuit 53 to a low (L) level signal, which is given to the AND circuit 54. Accordingly the AND circuit 54 inhibits passage of the trigger pulse from the switch 48. If forced circulation is not set, and the heart is repeating contraction with a period of within 2 seconds, the output of the OR circuit 52 is at L level, and the output of the NOT circuit 53 is at H level. In this case, the trigger pulse from the generating circuit 46 or 47 passes through the AND circuit 54 and is fed to the delay circuit 57 through the OR circuit 56. The AND circuit 55 prevents passage of the trigger pulse from the generator 44.

The delay circuit 57 delays the trigger pulse fed thereto for a predetermined period of time. This is of importance during spontaneous circulation. In the case of spontaneous circulation, the pump 14 for supplying the blood assists the heart of the patient in supplying the blood, so that the two blood supplies must be in synchronism. It is preferable that the pump 14 supply the blood with a time delay after the arterial blood is supplied by the heart. This is termed "counter pulsation." The delay circuit 57 determines this delay time, which is preferably so determined as to be dependent on the period of systole of the heart. The delay time is obtained, for example, by multiplying the previous period of systole measured or the mean value of preceding periods of systole by a suitable percentage. The measurement of the period and the calculation of the delay time can of course be performed automatically by a control circuit (not shown). The percentage is variable as desired.

The width of the delayed trigger pulse is shaped to resemble the systole time of the heart by a pulse width setting circuit 58. The control pulse delivered from the circuit 58 is sent through AND circuits 59 and 60 to the electromagnetic valve 31 to open the valve. The valve 31, when opened, permits supply of compressed air to the pump 14 to contract the pump 14 and supply the blood. Accordingly the width of the output pulse of the circuit 58 determines the contraction time of the pump 14. Preferably the contraction time corresponds to the systole time of the heart. The pulse width is calculated also based on the period of systole of the heart. In the case of forced circulation, the delay time of the circuit 57 and the pulse width of the circuit 58 are determined preferably in accordance with the heart rate set by the generator 44.

The AP is used also for controlling the start and discontinuance of the operation of the pulsatile pump 14. The AP signal from the blood pressure transducer 42 is applied to a peak hold circuit 61 and a mean value calculating circuit 62. While the heart of the patient is in operation and also while the pump 14 is in operation, the arterial blood is pulsating. Accordingly the AP signal has a pulsatile waveform. The peak value of the pulsatile AP signal, corresponding to the systolic value of the arterial blood pressure, is held by and sent out from the hold circuit 61. The systolic pressure signal is fed to an upper limit detecting circuit 63 and a lower limit detecting circuit 64. An upper limit value (e.g. 150 mm Hg) for the systolic pressure is set on the upper limit detecting circuit 63. When the systolic pressure input signal is in excess of the upper limit value, the circuit 63 emits an H level signal. A lower limit value (e.g. 100 mm Hg) for the systolic pressure is set on the lower limit detecting circuit 64. If the systolic pressure input signal is below the lower limit value, the circuit 64 delivers an H level signal. The upper limit value and the lower limit value are variable.

The detecting signal from the upper limit detecting circuit 63 is sent through an OR circuit 67 to the set input terminal of a flip-flop 69. The detecting signal from the lower limit detecting circuit 64 is sent through an OR circuit 68 to the reset input terminal of the flip-flop 69. The flip-flop 69 is initially reset. When the flip-flop 69 is reset, the inverted output thereof is at H level, and at this time, the control pulse of the circuit 58 is sent through the AND circuit 59 to the valve 31. When the flip-flop 69 is set, the inverted output thereof is at L level, so that the passage of the control pulse is prevented. Consequently the pump 14 is brought out of operation when the highest AP value exceeds the upper limit value, whereas the pump 14 is initiated into operation when the value drops below the lower limit value. The highest AP value is always maintained at a level between the upper limit value and the lower limit value.

While the pump 14 is held out of operation, no peak appears in the AP signal. When the blood supply pump is not a pulsatile pump but a rotary pump, the blood is continuously forced into the artery of the patient, so that no peak appears in the AP signal. The mean value calculating circuit 62 is provided to meet such a situation. The peak hold circuit 61 has the function of producing a no-peak signal when no pulse appears in the AP signal for a specified period of time. The no-peak signal is applied to the calculating circuit 62, whereupon the circuit 62 functions to calculate and deliver the mean value of the AP signal every specified period of time. The mean value signal is sent to upper and lower limit detecting circuits 65 and 66, on which upper and lower limit values are set respectively. When the mean value signal exceeds the upper limit value and when the signal drops below the lower limit value, the circuits 65 and 66 each produce an H level detecting signal, which is fed to the flip-flop 69 in the same manner as above.

The detecting signal (H level) from the sensor 24 of the CVP adjusting unit 20 has its waveform shaped by a waveform shaping circuit 73 and then applied to the set input terminal of a flip-flop 74. The VP signal from the blood pressure transducer 41 is fed to a mean value calculating circuit 71, in which the mean value thereof is calculated every specified time interval. The mean value signal is delivered to a lower limit detecting circuit 72, on which a lower limit value for the venous blood pressure is set. When the mean VP value drops below the lower limit value, the circuit 72 emits an H level detecting signal, which is given to the reset input terminal of the flip-flop 74. The flip-flop 74 is initially reset. While the flip-flop 74 is reset, the inverted output signal thereof is at H level. The H level signal opens the electro-magnetic valve 32. When the flip-flop 74 is set by an overflow detecting signal from the sensor 24, the flip-flop delivers an inverted output at L level to close the valve 32. Consequently the pump 11 withdraws an increased amount of blood as already described. Thus, if the CVP exceeds the upper limit level (e.g. 10 to 20 mm Hg), for example, due to the congestion of blood in the body, the valve 32 closes, whereas if the mean VP value drops below the lower limit value (e.g. several mm Hg), the valve 32 opens. The CVP is therefore maintained at an approximately constant level at all times.

The blood pressure transducer 41 and the circuits 71 and 72 are not always necessary; the valve 32 may be controlled only with the detecting signal of the sensor 24. In this case, the electromagnetic valve 32 is held open at all times and is closed only while the sensor is detecting an overflow, whereby the CVP can be kept approximately constant if the upper limit for the CVP is set at a suitable level.

The detecting signals from the sensors 25 and 26 are fed to a valve control circuit 81. When the sensor 25 detects that the blood in the reservoir has reduced to below a specified level, the circuit 81 emits an H level signal to open the valve 33 until the sensor 26 gives an upper limit level detecting signal. The H level signal is sent through a NOT circuit 82 to the AND circuit 60. Accordingly when the blood remaining in the reservoir is found to be in a small amount, the control pulse from the circuit 58 does not pass the AND circuit 60, and the motor 14 comes to a stop. This prevents air from flowing into the artery of the patient. However, if the level to be detected by the sensor 25 is set at a relatively high level, the pump 14 need not always be stopped even if the sensor 25 emits a detecting signal.

Figure 6:
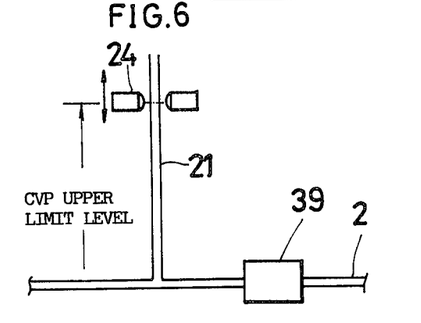

FIGS. 4, 5 and 6 show other examples of CVP adjusting units. With reference to FIG. 4, a vertical tube 21 has an extension 21a extending vertically beyond the portion thereof communicating with a vertical tube 22. The extension 21a communicates at its upper end with the tube 22. When the CVP increases abruptly beyond its upper limit level, the pressure in excess of the upper limit level can be measured by the extension 21a. A sensor 24 may be disposed in the vicinity of the communicating portion of the vertical tube 21.

FIG. 5 shows pairs of vertical tubes 21A, 22A; 21B, 22B; and 21C, 22C. The vertical tubes 21A to 21C have communicating portions at different levels. The other vertical tubes 22A to 22C are provided with sensors 24A to 24C for detecting an overflow of the blood, respectively. A plurality of CVP measuring levels can be set on this CVP adjusting unit. When the detecting signals from the sensors 24A to 24C are used for controlling the opening degree of the valve 32, the CVP is controllable in a finer more accurate manner. With the arrangement of FIG. 5, the vertical tubes 22A, 22B are provided with electromagnetic valves 38A, 38B, respectively. These valves 38A, 38B are open usually and are closed when the corresponding sensors 24A, 24B have detected an overflow of blood. The valves are opened again when the CVP lowers to eliminate the overflow.

The overflow line 2 shown in FIG. 6 is provided only with a vertical tube 21 the upper end of which is open to the atmosphere. The line 2 has an electromagnetic valve 39 positioned closer to the pump 12. The vertical tube 21 is fixed in place, while a sensor 24 is movable upward or downward along the tube 21 as supported on the tube. The valve 39 is closed usually but is opened when the sensor 24 detects the blood reaching the level of the sensor. Thus the blood is aspirated through the line 2 as is the case with an overflow. The upper limit level for the CVP is settable as desired by varying the level of the sensor 24.

Figure 7:
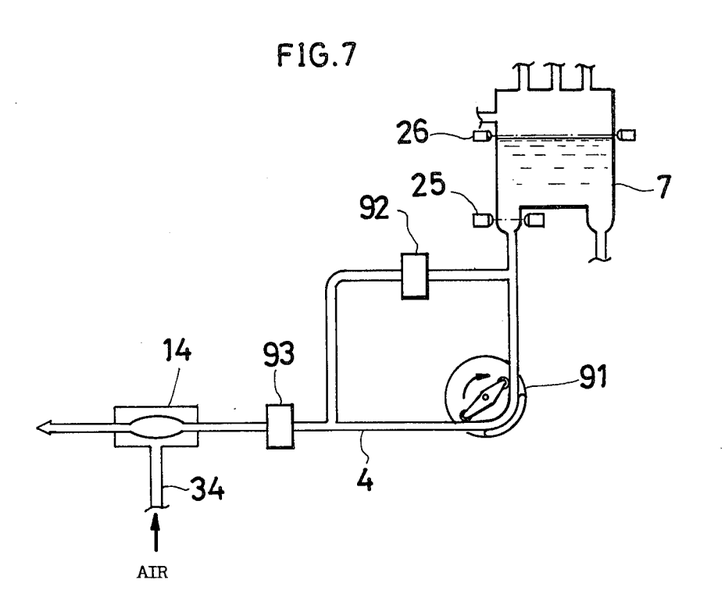
FIG. 7 shows another example of blood supply line.

FIG. 7 shows another example of blood supply line. Between a blood reservoir 7 and a pump 14, the blood supply line 4 is provided with a rotary pump 91 and an electromagnetic valve 93 positioned downstream from the pump 91. In parallel with the rotary pump 91, a return line is connected to the line 4, with another electromagnetic valve 92 provided on the return line. For forced circulation, the pumps 91, 14 operate, and the valve 92 is closed with the valve 93 opened, whereby the blood in the reservoir 7 is aspirated by the pump 91 and intermittently forced out by the pump 14. If the highest AP value exceeds an upper limit value, the valve 92 is opened and the valve 93 is closed, so that the blood circulates through the return line and the pump 91 without flowing into the pump 14. At this time, the pump 14 may be in or out of operation. When the highest AP value drops below a lower limit value, the valve 92 is closed again and the valve 93 is opened.

While the heart of the patient is in operation to circulate the blood spontaneously, the pressure of the left atrium (hereinafter referred to as "LAP") can be measured. Accordingly the blood circulation can be so controlled that the left side system of the heart and the right side system of the heart will function in good balance. The LAP reflects the function of the left heart system, while the CVP reflects the function of the right heart system. The range of desired values of LAP (e.g. 8 to 15 mm Hg) is predetermined, and the CVP is so adjusted that the LAP will be maintained in this range at all times.

Figure 8:
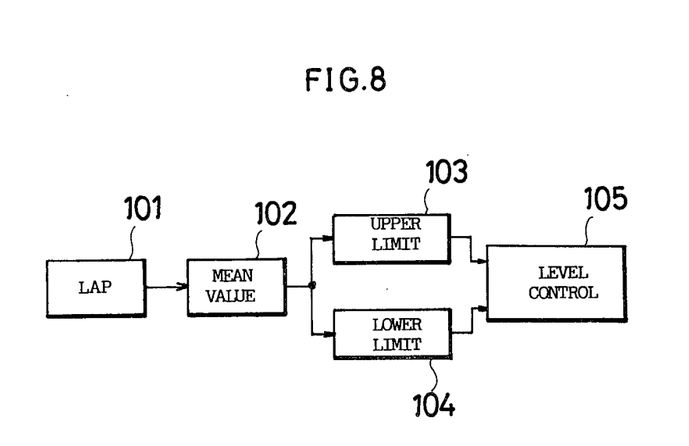
FIG. 8 is a block diagram showing a system for adjusting the pressure of the left atrium.

With reference to FIG. 8, the LAP is detected by a pressure transducer 101. The means LAP value is calculated at a specified time interval by a mean value calculating circuit 102. The upper limit value (e.g. 15 mm Hg) of the desired range of LAP values is set on an upper limit detecting circuit 103. When the output from the circuit 102 exceeds the upper limit value, the circuit 103 emits an upper limit detecting signal. The lower limit value (e.g. 8 mm Hg) of the desired LAP range is set on a lower limit detecting circuit 104. When the LAP drops below the lower limit value, the circuit 104 emits a lower limit detecting signal. Level control means 105 raises or lowers the upper limit level of CVP in the CVP adjusting unit 20. With the unit 20 shown in FIG. 1, the vertical tubes 21, 22 and the support member 23 are raised or lowered. With the arrangement shown in FIG. 6, the blood sensor 24 is raised or lowered. When the detecting LAP value is above the upper limit setting, the upper limit level for CVP is slowly lowered until the LAP lowers below the upper limit value. Conversely if the detected LAP value is below the lower limit, the upper limit level for the CVP is slowly raised. The rise of the CVP upper limit level is stopped when the LAP exceeds the lower limit value. In this way, the LAP is maintained in the desired range at all times.

What is claimed is:

1. In an extracorporeal blood circulation system including:
   a blood withdrawing line,
   an artificial lung provided on the line,
   a reservoir for the blood withdrawn,
   a blood supply line for sending out the blood from the reservoir, and
   a blood supply pump provided on the blood supply line; an apparatus for adjusting the amount of blood to be withdrawn comprising:
   means for detecting that the venous pressure has exceeded a predetermined upper limit level,
   a blood withdrawing pump provided on the blood withdrawing line, a shunt line connecting the reservoir to the inlet side of the blood withdrawing pump, a valve provided on the shunt line and usually open, and a valve control circuit for closing the valve when the venous pressure has exceeded the upper limit level.

2. An apparatus as defined in claim 1 wherein the venous pressure detecting means comprises a vertical tube having an upper end opened to the atmosphere and a blood sensor provided at a position of specified height for the vertical tube for detecting that the blood level has reached the position.

3. An apparatus as defined in claim 1 wherein the venous pressure detecting means comprises two vertical tubes communicating with each other at their upper ends and movable upward or downward, and a blood sensor for detecting the blood flowing over the communicating portion from one of the vertical tubes to the other, at least one of the vertical tubes being opened to the atmosphere at its upper end.

4. An apparatus as defined in claim 1 wherein the venous pressure detecting means comprises a blood pressure transducer and an upper limit detecting circuit for detecting that the output of the blood pressure transducer has exceeded the predetermined upper limit level.

5. An apparatus as defined in claim 1 wherein the venous pressure is the central venous pressure.

6. A system for controlling a pulsatile pump provided on an extracorporeal circulation line, the system comprising means for generating a trigger pulse upon detecting contraction of the heart of a patient for spontaneous circulation, a circuit for generating a trigger pulse in accordance with a heart rate set for forced circulation, means for selecting one of the trigger pulses, and means for driving the pulsatile pump in response to the selected trigger pulse.

7. A system as defined in claim 6 wherein the trigger pulse generating means for spontaneous circulation comprises a blood pressure transducer for measuring the arterial pressure, and a circuit for generating a trigger pulse in synchronism with a pulse waveform in the output signal of the blood pressure transducer.

8. A system as defined in claim 6 wherein the trigger pulse generating means for spontaneous circulation comprises an electrocardiograph and a circuit for generating a trigger pulse in synchronism with an R wave in the output signal of the electrocardiograph.

9. A system as defined in claim 6 wherein the trigger pulse generating means for spontaneous circulation comprises a blood pressure transducer for measuring the arterial pressure, a circuit for generating a first trigger pulse in synchronism with a pulse waveform in the output signal of the blood pressure transducer, an electrocardiograph, a circuit for generating a second trigger pulse in synchronism with an R wave in the output signal of the electrocardiograph, and a switch for selecting one of the first and second trigger pulses.

10. A system as defined in claim 6 wherein the trigger pulse selecting means comprises a switch for selecting spontaneous circulation or forced circulation, a compensation circuit for producing a signal for selecting forced circulation upon detecting that the trigger pulse based on spontaneous circulation is not repeated even after the lapse of a specified period of time, and a preference circuit for permitting the selection of forced circulation by the compensation circuit in preference to the selection by the selecting switch.

11. In an extracorporeal blood circulation system including a blood withdrawing line, an artificial lung provided on the line, a reservoir for the blood withdrawn, a blood supply line for sending out the blood from the reservoir, and a blood supply pump provided on the blood supply line heart, an apparatus for adjusting the pressure of the left atrium comprising:
  means for detecting that the venous pressure has exceeded an upper limit level,
  means for increasing the amount of blood to be withdrawn when the venous pressure has exceeded the upper limit level,
  means for detecting the pressure of the left atrium, and
  means for varying the upper limit level for the venous pressure in accordance with the pressure of the left atrium to maintain the pressure of the left atrium in a predetermined range.

12. A system for circulating the blood extracorporeally comprising:
  a blood withdrawing line,
  an overflow line,
  a reservoir for the blood withdrawn and overflowed,
  a pump for leading the overflow of blood into the reservoir,
  a cannula comprising an outer tube having a slightly tapered forward end being formed with a number of holes and rear end connected to the withdrawing line, and an inner tube having a forward end being opened at the forward end of the outer tube and rear end extending outward from the outer tube, and
  blood overflowing means having two vertical tubes communicating with each other at their upper ends, at least one of the vertical tubes being opened to the atmosphere at its upper end, wherein one of the vertical tubes being connected at its lower end to the rear end of the inner tube of the cannula and the other being connected at its lower end to the overflow line.

13. A system as defined in claim 12, comprising:
  said two cannulae, and
  means for adjusting the central venous pressure comprising said blood overflowing means,
  wherein the outer tubes of said cannulae being connected at their rear ends of the withdrawing line and the inner tubes of said cannulae being connected at the inner tubes of said cannulae being connected at their rear ends to said one of the vertical tube of said blood overflowing means.

14. A system as defined in claim 12 wherein the two vertical tubes of said blood overflowing means are moveable upward or downward.

15. A system as defined in claim 12 comprising:
  a blood sensor for detecting the blood flowing over the communicating portion from one of the vertical tubes to the other of said blood overflowing means,
  a blood withdrawing pump provided on the blood withdrawing line,
  a shunt line connecting the reservoir to the inlet side of the blood withdrawing pump,
  a valve provided on the shunt line and usually open, and
  a valve control means for closing the valve when the blood sensor has detected the overflow of blood.

16. A system as defined in claim 12, comprising:
  a blood supply line for sending out the blood from the reservoir,
  a blood supply pump provided on the blood supply line,
  a blood pressure transducer for measuring the arterial pressure,
  an upper limit detecting circuit for detecting that the arterial pressure has exceeded a predetermined upper limit value,
  a lower limit detecting circuit detecting that the arterial pressure has lowered below a predetermined lower limit value, and
  a control circuit for stopping the blood supply pump upon detecting the upper limit and for operating the blood supply pump upon detecting the lower limit.

17. A system as defined in claim 16 wherein the blood supply pump is a pulsatile pump.

18. A cannula for use in an extracorporeal blood circulation system comprising an outer tube having a slightly tapered forward end being formed with a number of holes and rear end, and an inner tube having a forward end being opened at the forward end of the outer tube and rear end extending outward from the outer tube.

* * * * *